United States Patent [19]

Hanson et al.

[11] 4,327,709

[45] May 4, 1982

[54] APPARATUS AND METHOD FOR THE PERCUTANEOUS INTRODUCTION OF INTRA-AORTIC BALLOONS INTO THE HUMAN BODY

[75] Inventors: Bruce L. Hanson, Wayne, N.J.; Sidney Wolvek, Brooklyn, N.Y.

[73] Assignee: Datascope Corp., Oakland, N.J.

[21] Appl. No.: 86,150

[22] Filed: Oct. 18, 1979

Related U.S. Application Data

[63] Continuation-in-part of Ser. No. 883,513, Mar. 6, 1978, Pat. No. 4,261,339.

[51] Int. Cl.³ .......................................... A61M 29/02
[52] U.S. Cl. ................................. 128/1 D; 128/344; 128/349 B; 128/DIG. 16
[58] Field of Search .................... 128/349, 349 B, 347, 128/348, 214.4, DIG. 16, 344, 1 D

[56] References Cited

U.S. PATENT DOCUMENTS

| | | | |
|---|---|---|---|
| 3,504,662 | 4/1980 | Jones | 128/1 |
| 3,680,544 | 8/1972 | Shinnick et al. | 128/348 X |
| 3,692,018 | 9/1972 | Goetz et al. | 128/1 |
| 3,837,347 | 9/1974 | Tower | 128/404 |
| 3,877,838 | 4/1975 | Choy | 128/1 D |
| 3,900,033 | 8/1975 | Leininger | 128/344 |
| 3,903,885 | 9/1975 | Fuchs | 128/DIG. 16 |
| 3,939,820 | 2/1976 | Grayzel | 128/1 D |
| 3,978,863 | 9/1976 | Fettel et al. | 128/348 |
| 3,993,079 | 4/1976 | de Gatztanondo | 128/214.4 X |

FOREIGN PATENT DOCUMENTS 2456980 6/1976 Fed. Rep. of Germany .
955490 4/1964 United Kingdom .

OTHER PUBLICATIONS

Desilets–Hoffman Technique, "A New Method of Percutaneous Catheterization", Radiology, 85 (1965), pp. 147–148.

Journal of the American Medical Association, Jan. 31, 1977, vol. 237.

Cordis, "Cordis Ducor Accessories to the Angiographic System".

*Primary Examiner*—Stephen C. Pellegrino
*Attorney, Agent, or Firm*—Darby & Darby

[57] ABSTRACT

Apparatus and method for the percutaneous insertion of intra-aortic balloons into the human body wherein a sheath is provided which can be inserted into an artery through a puncture, and an intra-aortic balloon of a size sufficiently small and having sufficient flexibility is used which can be moved through the sheath into the artery. The apparatus and method includes, puncturing the skin into the artery until a needle means having a bore, introducing a guide wire into the artery through the needle means, advancing a dilator-sheath set over the wire to enlarge the puncture and to place an end of the sheath within the artery, withdrawing the dilator and guide wire and then inserting the balloon through the sheath.

23 Claims, 6 Drawing Figures

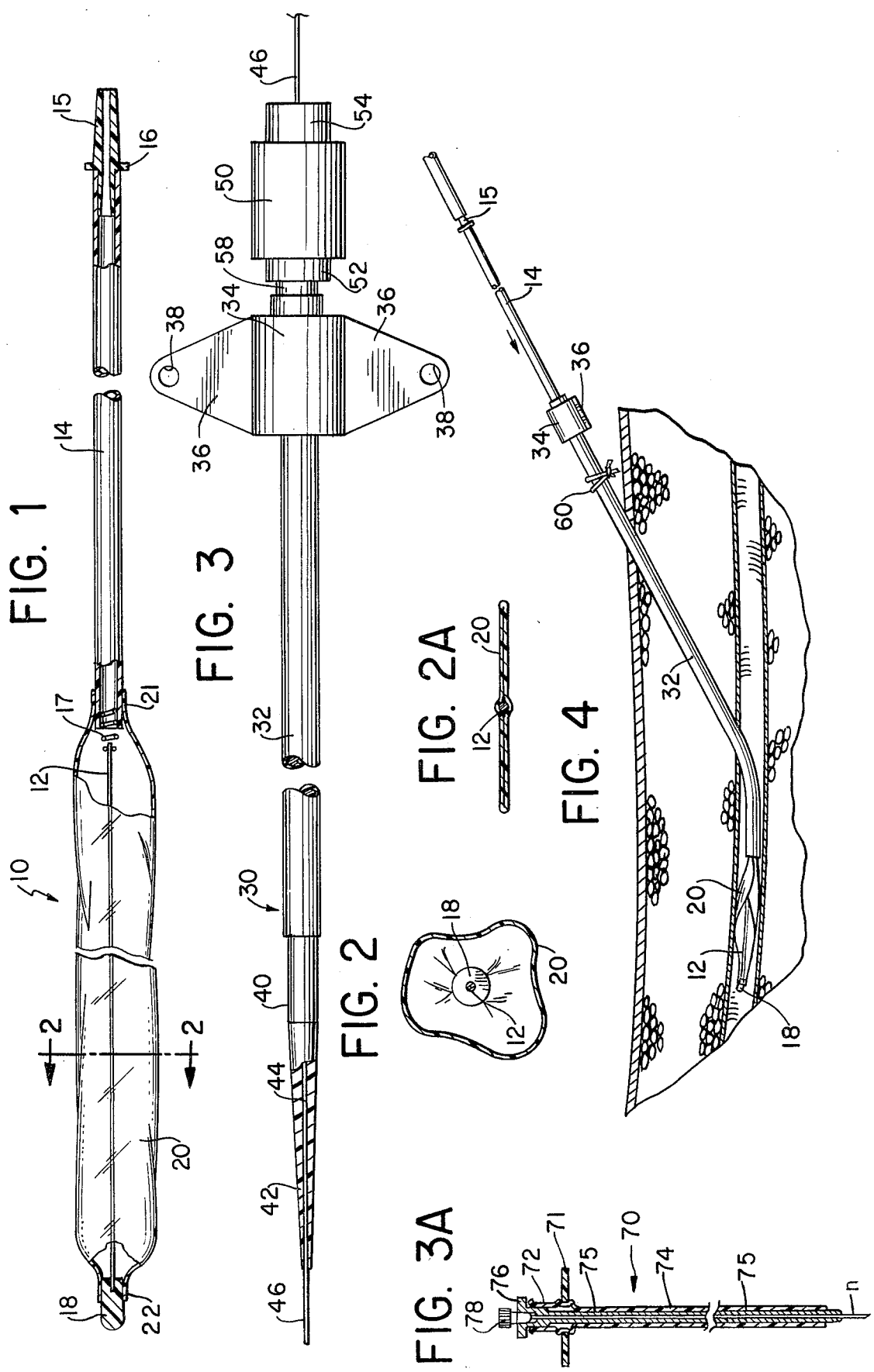

APPARATUS AND METHOD FOR THE PERCUTANEOUS INTRODUCTION OF INTRA-AORTIC BALLOONS INTO THE HUMAN BODY

RELATED APPLICATION This application is a continuation-in-part of our prior co-pending application Ser. No. 883,513, filed Mar. 6, 1978, now U.S. Pat. No. 4,261,339 entitled Balloon Catheter With Rotatable Support, which is assigned to the same assignee.

BACKGROUND OF THE INVENTION

This invention relates to an apparatus and method for the percutaneous introduction of intra-aortic balloons into the human body, including an intra-aortic balloon which can be introduced percutaneously.

In the use of intra-aortic ballons, the balloon must be positioned within aorta. In general, the balloons are formed as part of a catheter.

Intra-aortic balloon pumping is a recognized technique for cardiac assistance for a failing heart. It is also a recognized technique cardiogenic shock. Further, it has been used for such purposes as helping to wean a patient away from cardiopulmonary bypass, to support a patient during a difficult postoperative period, and to provide a pulsatile flow through the linear flows supplied by the cardiopulmonary bypass device. Intra-aortic balloon pumping has also been used therapeutically after myocardial infarction to limit the extension of necrosis and it also has been used as a therapy for angina pectoris.

The intra-aortic balloon catheters of the prior art are relatively stiff and bulky and have a large "entering" cross section, i.e. the size of the opening needed to pass the balloon into the body.

The femoral artery has heretofore been used for insertion of the prior art balloon catheters because of the large diameter of that artery. However, due to the large entering cross-sections of the prior art balloons, considerable and rather delicate surgery must be performed in order to reach and isolate the femoral artery in a manner which enables the balloons to be introduced. In many cases, only cardio-pulmonary surgeons are willing or able to undertake this surgery, thus limiting the use of the otherwise advantageous balloon. Further, considerable difficulty is often encountered in the healing of these surgical incisions because of their location in the groin.

Additionally, the stiffness of prior art balloon devices along their lengths prevents precise maneuverability of the catheter within the vascular structure and thereby limits their potential for efficacy.

In our aforesaid prior application, a balloon is provided of a reduced cross-section whose ends may be connected to be rotated relative to each other, or to the catheter to twist, or wind, the balloon around a central shaft. However, this approach gives rise to the formation of oblique wrinkles on the wrapped profile exposing the interior walls of the artery to said wrinkles thereby making it somewhat more difficult to insert the balloon and dependent on complete unwrapping to achieve efficacy.

SUMMARY OF THE INVENTION

The present invention is directed to an improved apparatus and method for the insertion of an intra-aortic balloon into the arterial system of a patient without the need for exposing the artery of a patient. This is accomplished by inserting the balloon through the skin, i.e., percutaneously.

OBJECTS OF THE INVENTION

It is therefore an object of the present invention to provide an apparatus and method for the percutaneous insertion of an intra-aortic balloon.

Another object is to provide an apparatus with a very small "entering" cross section to allow percutaneous insertion of a intra-aortic balloon without the need for a surgical incision in the groin or elsewhere.

Still another object is to provide an intra-aortic balloon apparatus that is flexible enough, while still maintaining support for an intra-aortic balloon, to provide precise maneuverability within the vascular structure to allow entry into and guidance through a tortuous and sometimes restricted passage.

A further object is to provide an intra-aortic balloon that does not present the oblique wrinkles of a wrapped profile to the edges or to the interior of the artery into which it is inserted.

Another object is to provide a method and apparatus for inserting an intra-aortic balloon rapidly and easily into an artery without requiring the special skills of a cardiovascular surgeon.

These and other objects of the invention are accomplished by providing a system of components including an intra-aortic balloon, a percutaneous catheter insertion set which includes a hollow needle and guide wire, a dilator and a vascular sheath. The balloon is constructed in a manner, with a small entering cross-section and being very flexible, to make it especially suitable for use in the percutaneous insertion.

The system is utilized by making a puncture with the hollow needle through the skin of a patient into an artery, inserting a guide wire through the needle, withdrawing the needle while leaving the guide wire, inserting the dilator and the sheath into the artery, removing the dilator portion and inserting the intra-aortic balloon-catheter assembly through the sheath. The ballon-catheter assembly is constructed to have a small entering cross-section and to be relatively small and flexible so that it can be more easily guided through the arterial system.

Other objects and advantages of the present invention will become more apparent upon reference to the following specifications and annexed drawings in which:

DESCRIPTION OF THE DRAWINGS

FIG. 1 is an elevational view, partly in cross-section, of one embodiment of the intra-aortic balloon and catheter according to the present invention;

FIG. 2 is a cross-section along lines 2—2 of FIG. 1 showing the interior of the intra-aortic balloon;

FIG. 2A shows the balloon collapsed;

FIG. 3 is an elevational view, partly in cross-section of one embodiment of the introducer/sheath assembly;

FIG. 3A is an elevational view in cross-section of the needle for making the puncture; and FIG. 4 is a diagrammatic view showing insertion of the balloon catheter assembly into the artery through the protective sheath.

DESCRIPTION OF THE PREFERRED EMBODIMENTS

FIG. 1 illustrates a preferred embodiment of the intraaortic balloon 10 and catheter 14 of the invention. A thin and flexible support member 12, which is a thin wire of metal or plastic, has one end connected to the tip of a conically wound spring 17 by suitable means such as an adhesive, soldering or welding. Member 12 can be, for example, of stainless steel and has a diameter of about 0.025 inches. The length of the member 12 is selected to correspond approximately to the length of the balloon being used, a typical length being from about 8 to about 10 inches.

The catheter 14 is preferably of plastic material, such as polyurethane. A tapered piece 15 forming a Luer block fitting and having a stop shoulder 16 is attached to the free end of the catheter remote from spring 17. Piece 15 serves as the operating gas supply attachment fitting for the balloon.

The other end of support member 12 remote from spring 17 has a tip portion 18 of plastic material or other suitable material attached to it, for example, by an adhesive or by molding. The free end of the tip 18 is rounded and smooth since it is to be the lead portion of the balloon-catheter when inserted into the artery.

The balloon envelope 20 is of a suitable plastic material, such as polyurethane having a thickness in the range of from about 0.003 inches to about 0.0045 inches. The envelope 20 is of uniform diameter along its length except at the tapered ends. One end 21 of the envelope is sealed, such as by an adhesive or heat sealing, to the outer wall of catheter 14 adjacent the spring 17. The other end 22 is sealed, also by an adhesive or heat sealing, to the insertion tip 18.

The spaces between the turns of the winding of spring 17 constitute one large opening to enable rapid exchange of operating gas from catheter 14 to the interior of the chamber formed by the balloon envelope 20. Operating gas is supplied to end piece 15 of the catheter and enters the inflatable balloon chamber 20 from catheter 14 via the open areas of the spring. Supplying positive and negative gas pressures to the catheter end 15 controls the expansion and collapse of the envelope 20 and the chamber that it forms.

The thin support member 12 has enough resiliency and memory to support the balloon envelope. At the same time, it is thin enough to permit the balloon to pass through the comparatively narrow opening of a vascular sheath, to be described below. When a vacuum is applied to the interior of the balloon envelope 20 via catheter 14, the balloon envelope collapses and assumes a flat ribbon like geometry which permits its easy passage through the sheath and into the artery. FIG. 2 shows the cross-section of the balloon in an intermediate stage of collapse while FIG. 2A shows the balloon fully collapsed. When fully collapsed, the edges of the envelope can be folded as the balloon is inserted into the catheter, either up or down, back toward the support 12. This folding occurs naturally as the balloon is passed through the vascular sheath. The folding further reduces the width of the envelope and envelope surfaces extending essentially only longitudinally of the support member are present. That is, there is no twisting or wrapping of the envelope to present convoluted surfaces to the artery. The flexibility and resilience of support member 12, particularly since one end is flexibly mounted to spring 17, allows the balloon to be precisely maneuvered through the narrow and tortuous pathways of the human vascular system.

This balloon embodiment is intended only as illustrative and is not intended to limit the present invention, since it will be apparent to anyone skilled in the art that other embodiments may be fabricated. For example instead of a round wire support member 12, a flat support member of appropriate size can be utilized. Also the shape of spring 17 can be changed or any suitable coupling means that allows the rapid communication of operating gas between catheter 14 and balloon envelope 20 may be used.

FIG. 3 shows a preferred form of the sheath/dilator assembly 30. This assembly includes a tubular vascular sheath 32 which is formed of any thin biocompatible material such as, for example, TEFLON or polyethylene. One end of the sheath terminates in a molded hub 34, having extension tabs 36. These tabs have means, such as holes 38, which permit the hub, and consequently the sheath 32, to be attached to the body of the subject. The attachment can be carried out by suturing or surgically stapling the hub to the patient's body through the holes 38 or by taping the tabs to the patient's body with surgical tape.

The assembly includes a tubular dilator 40 having a tapered leading end 42 which has a sliding fit within the sheath 32. The dilator 40 is also made of a biocompatible material and preferably has a low coefficient of friction. A suitable material is TEFLON. The dilator has a passage, or bore 44, along its length through which a guide wire 46 can extend. Guide wire 46 is of any suitable material, for example, surgical grade stainless steel. The trailing end of the dilator remote from the tapered end 42 has a hub 50 with a reduced diameter neck area 52 and 54 at each end thereof. Illustratively, the sheath 30 has an outside diameter of about 0.178 inches and an inner diameter of about 0.161 inches. The outer diameter of the dilator is about 0.160 inches and the dilator bore 44 is about 0.039 inches.

The hub 50 of dilator 40 interlocks with the hub 34 of the sheath 32 by a suitable means such as a Luer lock taper 58. This permits both the sheath and the dilator to be inserted into the tissue of the patient's body and manipulated as a unit. Once inserted, the hubs can be separated and the dilator 40 removed, leaving only the sheath 32 within the patient's body.

The use of the system of FIGS. 1-3 is given with the insertion of the balloon being described illustratively with respect to percutaneous insertion in the femoral artery. While the balloon can also be percutaneously inserted into other areas of the body, insertion in the area of the femoral artery has been found to be easiest.

Initially, a needle is used to puncture the patient's skin, tissue and the wall of the femoral artery. One embodiment of the needle 70 is shown in FIG. 3A and is similar to an angiographic needle. This embodiment includes a hub 71 with neck 72 from which extends a flexible plastic cannula 74. A metal cannula 75 extends within plastic cannula 74 and has a head 76. A stylet 77 extends the length of and slightly beyond the end of the plastic cannula and has a head 78 above the head 76 of the metal cannula 75.

A technique similar to the Seldinger technique currently used in hospitals for the insertion of small angiographic catheters is preferably utilized. This is described in Radiology, November 1974, Volume 112, p.470 and in the Journal of The American Medical Association, January 31, 1977, Volume 237. The needle size can be in the order of 18 gauge. In general, the puncture is made by the stylet and the combined stylet metal cannula and plastic cannula are advanced as a unit. The stylet is withdrawn to verify arterial bleeding, after which the metal cannula is withdrawn, leaving only the flexible plastic cannula in the artery.

With the plastic cannula in the artery, as evidenced by the presence of arterial bleeding through the hub, the safety guide wire 46 is then inserted through the bore of the flexible plastic cannula and its end is guided through the cannula into the artery to a point beyond the aortic bifurcation. The guide wire 46 is also preferably coated with TEFLON or some other similar material to reduce friction and the potential for blood clot formation on the wire. The needle cannula is then removed, leaving only the safety guide wire with one end extending through the puncture and into the artery and the other end extending from the patient's body.

The sheath 32 and dilator 40 are assembled as a unit, as shown in FIG. 3, and the two hubs 34 and 50 are locked. The free end of the safety guide wire 46 which extends from the patient's body is then threaded into the bore 44 tapered end 42 of the dilator 40. The free end of the wire 46 is passed through the length of the dilator until it exits the end adjacent the hub 50.

The tapered end 42 of the dilator/sheath assembly is slipped down the wire 46 to the skin in the customary manner. This sheath/dilator set is then pushed into the puncture originally produced by the needle through the skin, subcutaneous tissue and the arterial puncture site. The Desilets-Hoffman technique, as described in "A New Method of Percutaneous Catheterization", Radiology, 85 (1965), pages 147–8, can be used for this. As the dilator is advanced into the puncture site, the size of the puncture increases. The insertion continues until the dilator has reached a point such that the leading end (left as shown in FIG. 3) of the sheath 32 is inserted into the artery. At this time, the dilator 40 and safety wire 46 are removed leaving only the sheath 32 in place within the patient's artery as shown in FIG. 4. Arterial bleeding can be controlled by finger pressure on the opening of the hub 34 or by pinching the portion of the sheath 32 extending from the tissue.

The intra-aortic balloon is now ready for insertion. A vacuum/gas supply line (not shown) is attached to the Luer fitting 15 at the end of the catheter. A vacuum is applied which collapses the balloon envelope 20 to assume a flat ribbon-like shape along the length of supporting wire, such as shown in FIG. 2A.

As shown in FIG. 4, the tip 18 of the balloon is then inserted into the opening of the tubular sheath 32 at the end adjacent the hub 34. The entire balloon is then advanced through the hub, sheath and into the artery by manipulating the balloon catheter 14. As the balloon enters and is advanced into the sheath it progressively folds longitudinally along its length. As it advances through the sheath, that portion of the balloon within the sheath stays folded longitudinally. The diameter of the tip 18 as well as the diameter of the catheter 14 is a very close fit within the internal diameter of the sheath 32. This close fit serves as a seal to blood and minimizes bleeding as the balloon progresses through the sheath. The flat ribbon-like configuration of the balloon membrane with the longitudinal folds is unencumbered by the slender support member 12 and is able to pass easily through the hub opening and the sheath 32, especially when aided by the lubricating effect of the blood within the sheath.

As the tip of the balloon exits from the end of the sheath within the artery, it begins to unfold to try to reassume the flat ribbon-like shape, since reduced air pressure is still being applied. This is shown in FIG. 4. The unfolding action progresses as more of the length of the balloon leaves the sheath. Complete unfolding of the balloon to a flat shape within the artery is not possible due to the constraint imposed by the arterial wall. The balloon catheter 14 is sufficiently long to permit the balloon to be advanced by the person inserting it along the length of the artery into the aorta (not shown) to a point where it can be left in place to achieve the necessary pumping action.

When the proper position in the aorta is achieved, with the balloon being entirely out of sheath 32, the balloon catheter can be secured to the sheath by a ligature 60 or by some other suitable means, and the sheath and/or the balloon catheter is suitably secured to the patient. Pumping and collapsing of the balloon to achieve the pumping action in the aorta is accomplished by control of the gas-vacuum supply source in a desired manner.

Withdrawal of the balloon from the body can be accomplished in one of two ways. First a vacuum can be applied to the balloon, as in insertion, and the balloon removed through the sheath, leaving the sheath in place for a possible exchange of balloons, for example a different size balloon, etc.

If no further balloon assistance is required, the balloon and sheath may be removed as a unit directly from the artery through the tissue and skin while leaving the sheath and other attachments in place on the catheter. Before doing this, sutures that may have been made through the sheath hub fastening means to the patient should first be severed. After withdrawal, manual pressure on the puncture site for a few moments is generally sufficient to stop the bleeding through the small hole left in the tissue.

As apparent, an apparatus and method has been provided for percutaneously implanting an intra-aortic balloon into a patient in which no vascular or other complicated surgery is necessary. Further, the balloon is of such a nature that it did not have to be wrapped or twisted or stretched in order to get it through a vascular sheath and into the arterial system. This also greatly enhances the ease of the implantation. The extreme slenderness and resiliency and flexibility of the support member 12 and the use of the flexible support wire allows precise maneuvering of the balloon within the tortuous vascular system allowing it to reach its proper pumping position.

Since the various components of the system are relatively inexpensive, this can be made disposable. This also facilitates use of the system and avoids the need for re-sterilization.

What is claimed is:

1. A system for percutaneous insertion of an intra-aortic balloon comprising in combination:
   a flexible hollow sheath having an end adapted to be inserted into an artery of a subject through a puncture,
   a balloon catheter comprising
   a catheter tube,
   a balloon envelope having one end connected to one end of said catheter tube, and
   an elongated flexible support member within said envelope having one end coupled to the other end of said envelope which is remote from said catheter tube, said envelope folding generally longitudinally along the axis of said support member to have a reduced diameter sufficiently small to be inserted through said sheath into the artery.

2. A system as in claim 1 wherein said balloon envelope folds longitudinally of the axis of said support member as it is inserted into said sheath.

3. An intra-aortic balloon as in claim 1 wherein said support member comprises a thin wire.

4. A system as in claim 1 wherein said connecting means also has passages for supplying gas to and exhausting gas from the interior of said envelope.

5. A system as in claim 4 wherein said connecting means is flexible.

6. A system as in claim 5 wherein said flexible connecting means comprises a spring.

7. An intra-aortic balloon as in claim 6 wherein said spring is helically wound, the gas passages being through the openings between the turns of the spring winding.

8. An intra-aortic balloon as in claim 7 wherein said spring is generally conical having a base and an apex, with said one end of said support member being connected to the apex of the conical spring and the base of the conical spring to said catheter tube.

9. A system as in claim 1 further comprising a dilator over which said sheath fits, said dilator having a tapered leading end which is advanced into the puncture to enlarge the puncture site.

10. A system as in claim 9 further comprising means for locking said sheath and dilator to move as a unit such that the advancement of the dilator into the puncture site also advances the sheath.

11. A system as in claim 9 wherein said dilator has a bore along its length and further comprising guide wire means for threading through said bore of said dilator, one end of said guide wire means being located in said opening to guide the advancement of the dilator into the puncture.

12. A system as in claim 11 further comprising means for locking said sheath and dilator to move as a unit such that the advancement of the dilator into the puncture site also advances the sheath.

13. A system as in claim 11 further comprising needle means to make the puncture of the skin and tissue of the patient to reach an artery, said needle means having a hollow bore through which the guide wire can move.

14. A system as in claim 1 wherein said one end of said envelope is sealed to said one end of catheter tube and said other end of said envelope is sealed to said one end of said elongated support member to form a chamber.

15. A system as in claim 14 further comprising means for coupling said other end of said support member to said one end of said catheter tube.

16. A method for the percutaneous insertion of an intra-aortic balloon into the artery of a patient comprising the steps of,
making a puncture through the skin and tissue of the patient to provide communication to the interior of an artery,
advancing a flexible sheath through the puncture to communicate with and to have a portion located within the artery, and
advancing an intra-aortic balloon catheter including a balloon envelope which is supported at least in part by a flexible support member which extends for a substantial portion of the length of the envelope with the envelope being folded generally longitudinally of said support member to reduce the diameter of the envelope for insertion through said sheath into the artery and through the artery to a desired location.

17. A method as in claim 16 wherein the step of advancing the sheath through the puncture further comprises providing a dilator and advancing the dilator into the puncture and artery ahead of the sheath.

18. A method as in claim 17 wherein the advancing of the sheath and dilator is carried out by advancing both as a unit.

19. A method as in claim 17 further comprising the steps of providing a guide wire which extends through the puncture into the artery and advancing the sheath and dilator over said guide wire.

20. A method as in claim 19 further comprising the steps of withdrawing the dilator and the guide wire before inserting the balloon catheter through said sheath.

21. A method as in claim 20 wherein the guide wire is introduced into the artery by making the puncture with a hollow needle whose end extends into the artery and advancing the guide wire into the artery through said hollow needle.

22. A method as in claim 19 wherein the guide wire is introduced into the artery by making the puncture with a hollow needle whose end extends into the artery and advancing the guide wire into the artery through said hollow needle.

23. A method as in claim 16 wherein the step of advancing the sheath comprises inserting a guide wire into the puncture and advancing the sheath over said guide wire.

* * * * *